(12) United States Patent
Tucker et al.

(10) Patent No.: US 7,271,137 B2
(45) Date of Patent: *Sep. 18, 2007

(54) DECONTAMINATION FORMULATIONS FOR DISINFECTION AND STERILIZATION

(75) Inventors: Mark D. Tucker, Albuquerque, NM (US); Daniel E. Engler, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/765,678

(22) Filed: Jan. 27, 2004

(65) Prior Publication Data

US 2005/0109981 A1    May 26, 2005

Related U.S. Application Data

(63) Continuation-in-part of application No. 09/952,940, filed on Sep. 14, 2001, now Pat. No. 6,723,890, which is a continuation-in-part of application No. 09/607,586, filed on Jun. 29, 2000, now Pat. No. 6,566,574, said application No. 10/765,678 is a continuation-in-part of application No. 10/251,569, filed on Sep. 20, 2002, said application No. 10/765,678 is a continuation-in-part of application No. 10/623,370, filed on Jul. 18, 2003, said application No. 10/765,678 is a continuation-in-part of application No. 10/740,317, filed on Dec. 18, 2003.

(60) Provisional application No. 60/446,642, filed on Feb. 10, 2003, provisional application No. 60/397,424, filed on Jul. 19, 2002, provisional application No. 60/387,104, filed on Jun. 7, 2002, provisional application No. 60/334,271, filed on Nov. 30, 2001, provisional application No. 60/326,508, filed on Oct. 1, 2001.

(51) Int. Cl.
| | |
|---|---|
| *A62D 3/00* | (2006.01) |
| *B01F 17/18* | (2006.01) |
| *B01F 17/38* | (2006.01) |
| *C11D 1/62* | (2006.01) |
| *C11D 3/39* | (2006.01) |

(52) U.S. Cl. ............... 510/110; 510/372; 510/504; 588/315; 588/320; 588/400; 588/401; 588/406; 588/408; 588/409; 588/901; 252/186.38; 252/186.41; 252/186.42; 252/186.39

(58) Field of Classification Search .............. 588/200, 588/218, 901; 252/186.38, 186.39, 186.41; 510/110, 370, 372, 502; 516/15
See application file for complete search history.

(56) References Cited

U.S. PATENT DOCUMENTS

| | | | | |
|---|---|---|---|---|
| 3,852,210 A | * | 12/1974 | Krezanoski | ................. 510/372 |
| 3,901,819 A | * | 8/1975 | Nakagawa et al. | ...... 252/186.4 |
| 4,536,314 A | * | 8/1985 | Hardy et al. | ................ 510/376 |
| 4,853,143 A | * | 8/1989 | Hardy et al. | ................ 510/312 |
| 5,116,575 A | | 5/1992 | Badertscher et al. | |
| 5,769,089 A | | 6/1998 | Hand et al. | |
| 5,859,064 A | | 1/1999 | Cronce | |
| 6,106,854 A | | 8/2000 | Belfer et al. | |
| 6,211,129 B1 | * | 4/2001 | Gladfelter et al. | .......... 510/294 |
| 6,245,957 B1 | * | 6/2001 | Wagner et al. | .............. 588/316 |
| 6,369,288 B1 | | 4/2002 | Brown | |
| 6,376,436 B1 | | 4/2002 | Cronce | |
| 6,448,062 B1 | * | 9/2002 | Huth et al. | ................. 435/264 |
| 6,455,751 B1 | | 9/2002 | Hoffman et al. | |
| 6,500,465 B1 | | 12/2002 | Ronlan | |
| 6,528,470 B1 | | 3/2003 | Ha et al. | |
| 6,566,574 B1 | * | 5/2003 | Tadros et al. | .......... 252/186.41 |
| 6,569,286 B1 | * | 5/2003 | Withenshaw et al. | ......... 162/72 |
| 6,569,353 B1 | | 5/2003 | Giletto et al. | |
| 6,589,565 B1 | | 7/2003 | Richter et al. | |
| 6,723,890 B2 | * | 4/2004 | Tucker et al. | ............... 588/318 |
| 2002/0132751 A1 | * | 9/2002 | Kohlus et al. | .............. 510/445 |
| 2003/0045767 A1 | | 3/2003 | Brown | |

FOREIGN PATENT DOCUMENTS

WO        WO 02/02192 A1 *   1/2002

\* cited by examiner

*Primary Examiner*—Joseph D. Anthony
(74) *Attorney, Agent, or Firm*—Robert D. Watson

(57) ABSTRACT

Aqueous decontamination formulations that neutralize biological pathogens for disinfection and sterilization applications. Examples of suitable applications include disinfection of food processing equipment, disinfection of areas containing livestock, mold remediation, sterilization of medical instruments and direct disinfection of food surfaces, such as beef carcasses. The formulations include at least one reactive compound, bleaching activator, inorganic base, and water. The formulations can be packaged as a two-part kit system, and can have a pH value in the range of 7-8.

6 Claims, No Drawings

DECONTAMINATION FORMULATIONS FOR DISINFECTION AND STERILIZATION

CROSS-REFERENCE TO RELATED APPLICATIONS

This application is a continuation-in-part application of U.S. patent application Ser. No. 09/952,940, entitled "Concentrated Formulations and Methods for Neutralizing Chemical and Biological Toxants", filed on Sep. 14, 2001 now U.S. Pat. No. 6,723,890, which is a continuation-in-part application of U.S. patent application Ser. No. 09/607,586, entitled "Formulations for Neutralization of Chemical and Biological Toxants", filed on Jun. 29, 2000, now U.S. Pat. No. 6,566,574, and the specifications thereof are incorporated herein by reference.

This application is also a continuation-in-part application of U.S. patent application Ser. No. 10/251,569, entitled "Enhanced Formulations for Neutralization of Chemical, Biological and Industrial Toxants", filed on Sep. 20, 2002 now pending, which claimed the benefit of the filing of U.S. Provisional Patent Application Ser. No. 60/326,508, entitled "DF-200—An Enhanced Formulation for Decontamination and Mitigation of CBW Agents and Biological Pathogens", filed on Oct. 1, 2001, and of U.S. Provisional Patent Application Ser. No. 60/334,271, entitled "Configurations for the Rapid Deployment of DF-200", filed on Nov. 30, 2001, and of U.S. Provisional Patent Application Ser. No. 60/387,104, entitled "Decontamination Formulations", filed on Jun. 7, 2002, and the specifications thereof are incorporated herein by reference.

This application is also a continuation-in-part application of U.S. patent application Ser. No. 10/623,370, entitled "Decontamination Formulation with Sorbent Additive", filed on Jul. 18, 2003 now pending, which claimed the benefit of the filing of U.S. Provisional Patent Application Ser. No. 60/397,424 entitled "Powdered Additive for DF-200," filed on Jul. 19, 2002, and the specifications thereof are incorporated herein by reference.

This application is also a continuation-in-part application of U.S. patent application Ser. No. 10/740,317, entitled "Granulated Decontamination Formulations," filed on Dec. 18, 2003 now allowed, by M. D. Tucker, which claimed the benefit of the filing of U.S. Provisional Patent Application Ser. No. 60/446,642 entitled "DF-200 Configurations for Special Applications", filed on Feb. 10, 2003, and the specifications thereof are incorporated herein by reference.

GOVERNMENT RIGHTS

The Government has rights to this invention pursuant to Contract No. DE-AC04-94AL85000 awarded by the U.S. Department of Energy.

BACKGROUND OF THE INVENTION

The present invention relates to decontamination formulations for disinfection and sterilization applications. In particular, the present invention is directed to aqueous formulations that include at least one reactive compound, bleaching activator, and inorganic base; and that allow the formulation to be pre-mixed and packaged as a two-part kit system. The aqueous decontamination formulations can be delivered in a wide variety of embodiments, including, but not limited to: foams, sprays, liquids, gels, fogs and aerosols.

Much of the background of decontamination formulations has been previously discussed in the related patent applications and patent listed above. Briefly, the formulations of the present invention fall generally into two families, designated "DF-100" and "DF-200." DF-100 formulations comprise, for example, a cationic surfactant (e.g., benzalkonium chloride) and a reactive compound (e.g., hydrogen peroxide mixed with potassium bicarbonate, which forms the highly reactive, negatively-charged nucleophillic species, hydroperoxycarbonate ($HCO_4^-$), which is a strong oxidant), that when mixed with water (e.g., tap water, well water, seawater, etc.) and exposed to a toxant, neutralizes that toxant. The solubilizing agent serves to effectively render the toxant susceptible to attack, while the reactive compound serves to attack and neutralize the toxant.

The second family of decontamination formulations, DF-200, are enhanced versions of DF-100. In DF-200, a bleaching activator (e.g., propylene glycol diacetate or glycerol diacetate) has been added to speed up reaction kinetics, improve performance, and eliminate the need for pH adjustment.

In both DF-100 and DF-200 decontamination formulations some of the ingredients must be stored separately in order to prevent premature chemical reaction before use. For example, hydrogen peroxide must be stored separately from the other ingredients prior to use, due to its high reactivity. This can be accomplished by packaging the formulation as a multi-part kit system (e.g., 2-part, 3-part or 4-part kits). For example, a two-part kit system can be used, comprising a relatively inert component (Part A), and an active component (Part B) that comprises the reactive compound. The bulk of the make-up water may be "pre-packaged" in one of the two containers, which allows for rapid deployment of the decontamination solution, without the need for providing extra water in the field. Alternatively, the make-up water (including seawater) can be separately provided in the field, which greatly reduces the weight of the pre-packaged kit components, making the kit easier to ship and store.

An example of a non-foaming DF-200 decontamination formulation is:

DF-200NF (Enhanced Formulation for No Foam Applications)

2% Benzalkonium Chloride (Cationic Surfactant)
2% Glycerol Diacetate [Diacetin] (Bleaching Activator)
3% Hydrogen Peroxide (Oxidant)
5% Potassium Carbonate (Base, pH Buffer, and Peroxide Activator)
88% Water
Note: The formulation should have a pH value between 9.6 and 9.85 after mixing.

Although DF-100 and DF-200 decontamination formulations have been found to be highly effective in a number of applications for decontamination of chemical warfare agents (e.g., Sarin, Soman, VX, and Mustard), biological warfare agents (e.g., anthrax and plague), and toxic industrial chemicals (e.g., cyanide and phosgene), there is considerable interest in expanding this technology for use in more routine disinfection and sterilization applications. Examples of these applications include disinfection of food processing equipment, disinfection of areas containing livestock, mold remediation, sterilization of medical instruments, and direct disinfection of food surfaces, such as beef carcasses.

DF-100 or DF-200 decontamination formulations are perfectly applicable for some of these proposed uses, such as for mold remediation or disinfection of livestock areas. However, DF-100 and DF-200 are less than desirable for the other proposed applications for two reasons. First, the application of DF-100 or DF-200 to a surface leaves a residue upon drying which needs to be rinsed before further use of certain items, such as food processing equipment or medical instruments. This residue is primarily caused by the cationic surfactant (e.g., benzalkonium chloride) that is used in some embodiments of the formulations. A second problem is that benzalkonium chloride is not approved for use on surfaces that will contact food unless it is used at very low concentrations (less than 400 mg/l), or unless it is thoroughly rinsed from the surface after use. The concentration of benzalkonium chloride in some embodiments of DF-100 or DF-200 decontamination formulations is approximately 20,000 mg/l in DF-200 and approximately 52,500 mg/l in DF-100. Both of these levels are well above the allowed concentration of 400 mg/l. Other ingredients in DF-200 (e.g., glycerol diacetate, hydrogen peroxide, potassium carbonate, water, etc.) are considered safe to be applied to food contact surfaces or directly to food surfaces.

As noted above, previous versions of DF-200 decontamination formulations generally have a pH in the range of 9.6-9.85 after mixing. The higher pH, while useful for neutralization of chemical toxants, is not necessary for kill of biological pathogens. For disinfection and sterilization applications, it would be generally desirable to have a lower pH value (i.e., less than 9, and preferably in the range of 7-8).

Some embodiments of DF-200 decontamination formulations are required to be packaged in three separate parts, which are mixed immediately before use. One reason that DF-200 is packaged as a three-component kit system is that it contains a novel bleaching activator (e.g., glycerol diacetate). Bleaching activators include compounds with O- or N-bounded acetyl groups, which react with strongly nucleophilic hydroperoxy anions (OOH$^-$) to yield peroxygenated species.

The peroxygenated species is a more efficient oxidizer than hydrogen peroxide alone. However, a fundamental problem with the use of a bleaching activator is that it must be stored separately from water (since it will hydrolyze over time in an aqueous solution); and it must be stored separately from hydrogen peroxide (to prevent the peroxygenation reaction) until just prior to use. Therefore, because Part A contains water and Part B contains hydrogen peroxide, the bleaching activator is packaged as a separate component, Part C. An example of a three-part kit configuration for DF-200 is shown below:

DF-200 (All-Liquid Three Part Kit Configuration)

Part A:
2.0 g Variquat 80MC (cationic surfactant)
1.0 g Adogen 477 (cationic hydrotrope)
9.0 g Propylene Glycol (solvent and anti-freeze)
0.4 g 1-Dodecanol (foam stabilizer)
0.8 g Diethylene Glycol Monobutyl Ether (solvent)
0.5 g Isobutanol (solvent)
0.2 g Celquat SC-240C (water soluble polymer for viscosity boosting)
5.0 g Potassium Carbonate (base and pH buffer)
0.2 g Potassium Bicarbonate (pH buffer)
30.9 g De-ionized Water Part B:
43.3 g of 8% Hydrogen Peroxide Solution (oxidizer)

Part C:
2.0 g Glycerol Diacetate [Diacetin] (bleaching activator)

Note: Mix Part B into Part A. Then mix Part C into Part A/B. The final pH (after mixing) should be between 9.6 and 9.8. Total=100 grams of activated solution.

Although the three parts of DF-200 in this example can be mixed together in a very short time, this three-part packaging requirement limits deployment options for the formulation. For example, it would be desirable to have the capability to deploy DF-200 in small hand-held spray bottles for personal use. Such a spray bottle could draw liquid formulation out of two separate chambers and conveniently mix the two liquids as they are sprayed. However, three-part kit configurations of DF-200 cannot be deployed using a two-component spray bottle.

Previous formulations of DF-100/DF-200 used a high pH (e.g., 9.6) to provide effective decontamination of certain chemical agents (e.g., VX). However, a high pH is not necessary for effective kill of biological pathogens. A more neutral, lower pH (e.g., 7.5-8.0) would be preferred for disinfection and sterilization applications that don't involve chemical agent decontamination.

Optionally, some or all of the various components/parts of a multi-part (e.g., 2-part or 3-part) kit system may be in the form of a dry, granulated, freely flowing powder that can be easily mixed with water that has been provided in the field. Such a dry powder material could be packaged with a desiccant for providing superior moisture protection, thereby extending the shelf life. Fortunately, one of the preferred reactive compounds, hydrogen peroxide, is available in a variety solid, granulated, water-soluble forms, including: urea hydrogen peroxide, sodium perborate, and sodium percarbonate.

Most of the other ingredients that are used in DF-100/200 formulations (e.g., cationic surfactants, cationic hydrotropes, solvents, peroxide activators, freeze point depressants, etc.) are typically available only in liquid form. Sorbent materials can be used to "dry-out" these liquid ingredients and convert them into a dry, granulated, freely-flowing powder that is more easily handled and mixed in the field, without affecting the neutralization performance of the made-up (i.e., "activated") decontamination solution.

An all-granulated (all-dry) decontamination formulation would have the following advantages over an all-liquid or part-liquid plus part-granulated formulations:
1. Significant reduction in the weight of the formulation required to be shipped and stored.
2. Saltwater or other low quality water can be used as the make-up water.
3. The formulation can be stored in low temperature locations.
4. Increased shelf life due to removal of water from the formulation.

Against this background, the present invention was developed.

SUMMARY OF THE INVENTION

The present invention relates to aqueous decontamination formulations that neutralize biological pathogens for disinfection and sterilization applications. Examples of suitable applications include disinfection of food processing equipment, disinfection of areas containing livestock, mold remediation, sterilization of medical instruments and direct disinfection of food surfaces, such as beef carcasses. The formulations include at least one reactive compound, bleaching activator, inorganic base, and water. The formulations can be packaged as a two-part kit system, and can have a pH value in the range of 7-8.

DETAILED DESCRIPTION OF THE INVENTION

The present invention addresses the need for decontamination formulations that neutralize the adverse effects of biological pathogens. Neutralization, disinfection, and sterilization are used interchangeably herein, and are defined as the mitigation, detoxification, decontamination, or otherwise destruction of biological pathogens to the extent that the biological pathogens no longer cause adverse effects to humans or animals. The formulation and described variations of the present invention can neutralize, and does not itself contain or produce, infection, significant adverse health effects, or even fatality in animals.

The word "formulation" is defined herein as the made-up, activated product or solution (i.e., aqueous decontamination solution) that is applied to a surface or body, dispersed into the air, etc. for the purpose of neutralization, with or without the addition of a gas (e.g., air) to create foam. Unless otherwise specifically stated, the concentrations, constituents, or components listed herein are relative to the weight percentage of the made-up aqueous decontamination solution. The word "water" is defined herein to broadly include: pure water, tap water, well water, waste water, deionized water, demineralized water, saltwater, or any other liquid consisting primarily of $H_2O$.

A minimum set of ingredients for an aqueous decontamination solution for disinfection and sterilization applications, according to the present invention, comprises:
  a reactive compound selected from the group consisting of nucleophilic compounds and oxidizing compounds;
  a bleaching activator;
  an inorganic base; and
  water.

Additional ingredients may optionally be added to the present invention, depending on the application and form of deployment. Some of the optional ingredients include: solubilizing compounds, cationic surfactants, cationic hydrotropes, solvents, fatty alcohols, freeze-point depressants, water-soluble polymers, foam stabilizers, pH buffers, corrosion inhibitors, sorbent additives for drying out liquid components, and combinations thereof.

Examples of suitable reactive compounds include: peroxide compounds, activated peroxide compounds (e.g., hydrogen peroxide+bicarbonate), hydrogen peroxide, urea hydrogen peroxide, hydroperoxycarbonate, sodium perborate, sodium percarbonate, sodium carbonate perhydrate, sodium peroxysilicate, sodium peroxypyrophosphate, sodium peroxysilicate, sodium peroxysilicatehydrogen, peroxide adducts of pyrophosphates, citrates, sodium sulfate, urea, sodium silicate, peracetic acid, oximates (e.g., butane-2,3-dione, monooximate ion, and benzohydroxamate), alkoxides (e.g., methoxide and ethoxide), aryloxides (e.g., aryl substituted benzenesulfonates), aldehydes (e.g., glutaraldehyde), peroxymonosulfate, Fenton's reagent (a mixture of iron and peroxide), sodium hypochlorite, and combinations thereof.

Use of these reactive compounds in the present invention can produce a variety of negatively-charged nucleophiles, e.g., hydroxyl ions ($OH^-$) and hydroperoxide ions ($OOH^-$) produced when using hydrogen peroxide; and/or hydroperoxycarbonate ions ($HCO_4^-$) produced when hydrogen peroxide is combined with a carbonate salt. Hydroperoxycarbonate ions ($HCO_4^-$) are much stronger oxidants than hydroxyl ions ($OH^-$) or hydroperoxide ions ($OOH^-$), and are especially effective in reacting with biological toxants.

As mentioned above, the reactive compound may comprise hydroperoxycarbonate ions ($HCO_4^-$), which are produced when hydrogen peroxide is combined with a carbonate salt in an aqueous solution. Examples of suitable carbonate salts include: potassium carbonate, potassium bicarbonate, sodium carbonate, sodium bicarbonate, sodium percarbonate ammonium bicarbonate, ammonium hydrogen bicarbonate, lithium bicarbonate, ammonium carbonate, and calcium carbonate. Addition of carbonate salts can also buffer the formulation to optimize the pH value.

Examples of suitable inorganic bases include: potassium carbonate, potassium bicarbonate, potassium hydroxide, potassium sulfate, potassium phosphate (dibasic or tribasic), potassium borate, potassium tetraborate, potassium acetate, sodium carbonate, sodium bicarbonate, sodium hydroxide, sodium sulfate, sodium phosphate (dibasic or tribasic), sodium borate, sodium acetate, ammonium carbonate, ammonium bicarbonate, ammonium hydroxide, ammonium sulfate, ammonium phosphate (dibasic or tribasic), ammonium borate, ammonium acetate, calcium carbonate, calcium bicarbonate, calcium hydroxide, calcium sulfate, calcium phosphate (dibasic or tribasic), calcium borate, calcium acetate, magnesium carbonate, magnesium bicarbonate, magnesium hydroxide, magnesium sulfate, magnesium phosphate (dibasic or tribasic), magnesium borate, magnesium acetate, sodium percarbonate, ammonium hydrogen bicarbonate and lithium bicarbonate, and combinations thereof. Some of these inorganic bases, such as potassium acetate, potassium carbonate, potassium bicarbonate and potassium phosphate (dibasic or tribasic), can also serve as a buffer for controlling and optimizing the pH value of the made-up decontamination solution.

Bleaching activators include compounds with O- or N-bounded acetyl groups or with nitrile groups that react with the strongly nucleophilic hydroperoxy anion ($OOH^-$) to yield peroxygenated species, which are more efficient oxidizers than hydrogen peroxide alone.

Since the 1950's, a number of different bleaching activators have been used in commercial laundry detergents, as well as other commercial products. The most common activators are tetraacetyl ethylenediamine (TAED), which is primarily used in Europe and Asia; and n-nonanoyloxybenzenesulfonate (NOBS), which is primarily used in the United States; and N-acetyl pentaacetate. NOBS is a proprietary chemical of the Proctor and Gamble Company. In a laundry detergent, hydrogen peroxide is provided in a solid form (usually as sodium perborate, which reacts in water to form the hydroperoxy anion). The addition of a bleaching activator greatly enhances the ability of a laundry detergent to remove stains from clothing.

It should be noted that TAED and NOBS bleaching activators are extremely insoluble in water (e.g., TAED is only 0.1% soluble at 25° C.). To get around this problem in a laundry detergent, the solid TAED or NOBS particles are kept in suspension by the agitating action of the washing machine, where they slowly react with the hydrogen peroxide in the detergent. However, agitating DF-200 solutions in the field presents practical problems; hence, water-soluble bleaching activators are preferred.

Examples of suitable water-soluble bleaching activators, according to the present invention, include: short-chained organic compounds that contain an ester bond (e.g., ethylene glycol diacetate), propylene glycol monomethyl ether acetate, methyl acetate, dimethyl glutarate, diethylene glycol monoethyl ether acetate, glycerol acetate (monoacetin), glycerol diacetate (diacetin), glycerol triacetate (triacetin), acetylcholine chloride, 4-cyanobenzoic acid, propylene glycol diacetate, and combinations thereof. A preferred activator is diacetin (glycerol diacetate). Another preferred water-soluble bleaching activator is propylene glycol diacetate (PGDA), which is shown below.

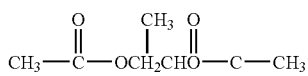

This molecule reacts with hydroperoxy anions (OOH⁻), giving up the ester bonds to form two peroxygenated molecules.

Propylene glycol diacetate (PGDA) also acts as an organic solvent that is highly effective in solubilizing insoluble organic molecules (e.g., chemical warfare agents, as well as foam stabilizers/boosters, such as 1-dodecanol and Lauramide DEA. Therefore, an added function of this compound is that it can be used to supplement the diethylene glycol monobutyl ether (DEGMBE) solvent that may be used in DF-100 and DF-100A formulations, or to supplement the di(propylene glycol) methyl ether solvent that may be used in some DF-200 formulations, thereby allowing the propylene glycol diacetate to serve a dual purpose (i.e., solvent and bleaching activator).

Bleaching activators are generally not stable in water for long periods of time. This is especially true when the aqueous solution is at a high pH (>10). Therefore, for long shelf life, the propylene glycol diacetate (or other bleaching activator) is preferably stored separate from the aqueous solution until use: This is not unlike other products that utilize bleach activators (e.g., laundry detergents), where all the components of the formulation are kept dry and separated until use (note: in the case of laundry detergent, the bleaching activator is encapsulated to prevent it from prematurely reacting with the peroxide component until both components are mixed in water).

Another example of a water-soluble bleaching activator is ethylene glycol diacetate, which also works well in DF-200 formulations. However, when ethylene glycol diacetate reacts with hydrogen peroxide it forms ethylene glycol (i.e., anti-freeze), which is a relatively toxic byproduct. Propylene glycol diacetate, on the other hand, does not form this relatively toxic byproduct.

Solid O-acetyl bleaching activators (e.g., acetylcholine chloride, which is often used in eye drop solutions),may be used in place of (liquid) propylene glycol diacetate. The chemical structure of this O-acetyl bleaching activator is shown below.

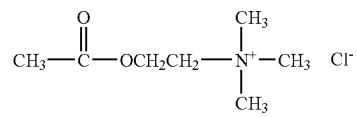

As can be seen, the molecule contains an O-acetyl group that can activate peroxide, and it is a quaternary compound, which is very compatible with DF-100/200 formulations. Acetylcholine chloride is also soluble in water, and is very hygroscopic.

Three other O-acetyl bleaching activators, monoacetin (glycerol monoacetate) diacetin (glycerol diacetate), and triacetin (glycerol triacetate) have also been tested for their effectiveness in DF-200 formulations. All of these compounds have also proven to be extremely effective bleaching activators. These compounds are water-soluble liquids.

Experiments have also shown that the peroxide in some DF-200 formulations is also effectively activated by a nitrile-containing compound, such as 4-cyanobenzoic acid (which is water-soluble), at a concentration of, for example, 2%, for the neutralization of both chemical agent and biological agent simulants.

The present invention may additionally comprise one or more solubilizing compounds. Examples of suitable solubilizing compounds include: cationic surfactants, cationic hydrotropes, ethanol, and combinations thereof.

Examples of suitable cationic surfactants include: quaternary ammonium salts and polymeric quaternary salts. Examples of suitable quaternary ammonium salts include: cetyltrimethyl ammonium bromide, benzalkonium chloride, benzethonium chloride, cetylpyridinium chloride, alkyldimethylbenzylammonium salt, tetrabutyl ammonium bromide, and combinations thereof. A preferred cationic surfactant is VARIQUAT 80MC™ (which used to be supplied by WITCO, Inc., but now is supplied by Degussa Goldschmidt). VARIQUAT 80MC™ comprises a mixture of benzyl (C12-C16) alkyldimethylammonium chlorides. A preferred concentration of quaternary ammonium salt used in these decontamination formulations is greater than about 0.1%, but less than about 10%, because at higher concentrations the quaternary ammonium salt becomes significantly toxic to humans and the environment.

Examples of suitable cationic hydrotropes include: tetrapentyl ammonium bromide, triacetyl methyl ammonium bromide, tetrabutyl ammonium bromide, and combinations thereof. A preferred cationic hydrotrope is ADOGEN 477™ (which used to be supplied by WITCO, Inc., but now is supplied by Degussa Goldschmidt). ADOGEN 477™ comprises pentamethyltallow alkyltrimethylenediammonium dichloride.

Ethanol may also be used as a solubilizing compound in the present invention because it is reported to have the capability to penetrate spore coats (Mechanisms of Killing Spores of *Bacillus subtilis* by Acid, Alkali and Ethanol, Setlow, B; Loshon, C A; Genest, P C; Cowan, A E; Setlow, C; Setlow, P, *Journal of Applied Microbiology*; 2002; v. 92, no. 2, p. 362-375). Ethanol is also safe for application to food contact surfaces. Additionally, some low molecular weight alcohols are not only solubilizers, but are also antimicrobial.

Examples of suitable fatty alcohols include alcohols having 8-20 carbon atoms per molecule, such as: 1-dodecanol, 1-tridecanol, hexadecanol, 1-tetradecanol, and combinations thereof.

Examples of suitable freeze point depressants include proplyene glycol, or inorganic salts, such as potassium acetate.

In foaming decontamination formulations, a cationic water-soluble polymer (e.g., Jaguar 8000™), may be used to increase the bulk viscosity of the solution and to produce a more stable foam. Some examples of suitable non-anionic water-soluble polymers include: polyvinyl alcohol, guar gum, (cationic or non-ionic) polydiallyl dimethyl ammonium chloride, polyacrylamide, glycerol, poly(ethylene oxide), poly(ethylene glycol), polyethylene glycol 8000 (e.g., PEG 8000), Jaguar 8000™ (Guar Gum 2-hydroxypropyl ether), polyquaternium compounds, and combinations thereof. A cationic polymer is preferred over a non-ionic polymer because anionic polymers do not work as well.

Fatty alcohols, i.e., 1-dodecanol, serve to increase the surface viscosity of the foam lamellae and to increase foam stability against drainage and bubble collapse. Other foaming agents may also be included in high-foaming formulations, namely Celquat SD 240c (at about 0.15%) and/or Lumulse Poly-Ethoxylated Glycerine (POE 12), at about 4%). POE-12 is a preferred additive because it allows for a broader range of workable temperature; it is liquid at room temperature, while others in this class are not. Polyethylene glycol polymer (PEG 8000) may be used for viscosity enhancement. This polymer is used in many cosmetics and is extremely soluble and stable in water. In addition, it is easier to mix into solution than Jaguar 8000 or a high molecular weight poly(ethylene oxide), since it does not have the tendency to clump.

In general, for any embodiments of the present invention, an acid or base may be added to the made-up decontamination solution, or to one of the Part A or Part B components, in order to adjust or buffer the final pH of the solution. Acid or base compounds may include, for example: KOH, citric acid, and HCL. Alternatively, sodium bisulfate (a common pool conditioning chemical), or other acid, can be used in place of citric acid to adjust the pH.

Corrosion inhibitors may be added to certain embodiments of the present invention to reduce their corrosivity. A preferred corrosion inhibitor is N,N-dimethyl ethanolamine. Other corrosion inhibitors, such as triethanolamine, ethanolamine salts of C9, C10, and C12 diacid mixtures, dicyclohexyl amine nitrite, and N,N-dibenzylamine, may also be used. The corrosion inhibitors added to DF-100/200 formulations can serve multiple purposes, including:

1. a corrosion inhibitor,
2. a pH buffer,
3. a solvent to keep 1-dodecanol in solution, and
4. a co-solvent to solubilize insoluble chemical agents, such as sarin or mustard.

Glycerol (glycerine) may be added to certain embodiments of the present invention as a viscosity builder (e.g., to replace Jaguar 8000, poly (ethylene oxide), or polyethylene glycol). Glycerol is a common ingredient in cosmetics, where it is used a viscosity builder, humectant, and emollient. Thus, the use of glycerol can serve multiple purposes:

1. viscosity builder,
2. a humectant (i.e., a substance which moisturizes the skin),
3. a solvent to keep 1-dedecanol in solution, and
4. a co-solvent to solubilize insoluble chemical agents, such as sarin or mustard.

A drawback to the use of glycerol is that it is solid at a fairly high temperature (below about 10° C.). Therefore, it would preferably be used in controlled temperature conditions (i.e., warm temperature conditions). Alternatively, ethoxylated forms of glycerol [e.g., poly(ethoxylated glycerol)] can be used. These forms of glycerol have a lower freezing point.

Sorbent additives optionally may be used to "dry out" one or more liquid ingredients of the aqueous decontamination formulation when pre-packaged in a multi-part kit system. A goal of "drying out" as many liquid ingredients as possible is to produce a dry, free-flowing, granulated powder or powders that can be placed in protective packaging (e.g., with a desiccant), have an extended shelf life, be more convenient to handle and mix in the field (as compared to handling and mixing a liquid), preferably not leave a residue, and have a reduced storage weight. In this way, the sorbent material acts as a drying agent to produce a granulated form.

The process of "drying out" liquid ingredients is not really an evaporation process as it is commonly understood. Rather, the sorbent additive absorbs and/or adsorbs the liquid to produce a powdered, free-flowing, granulated product that is easier to handle. Preferably, the sorbent additive should not contain any water, since some of the liquid ingredients will hydrolyze or degrade in the presence of moisture. Preferably, the sorbent additive is water-soluble so that it can be rapidly dissolved and mixed, and leave no residue.

Alternatively, a water-insoluble sorbent additive may be used (e.g., amorphous silica), if the presence of insoluble particles in the formulation is acceptable or desirable. For example, insoluble sorbent particles may be used to thicken and increase the viscosity of the made-up decontamination solution, effectively creating a gel that has increased "hang-time" on vertical surfaces. Alternatively, insoluble sorbent additives may be used as a cleaning solution and/or where an abrasive effect is desired. For some methods of application the presence of a sludge at the bottom of a container may not be a problem. However, the presence of insoluble sorbent particles in the made-up decontamination formulation may damage a pump mechanism, clog a spray nozzle, or leave an undesirable residue.

The sorbent additive is preferably finely ground to a small particle size so that a large effective surface area can be provided for adsorbing/absorbing the liquid ingredient(s). The sorbent additive preferably is chemically compatible with the entire family of DF-100/200 formulations, and should not cause degradation of the decontamination solution's effectiveness, or degrade the foaming properties (if a foaming version is being used). The sorbent additive may be selected from elements/ingredients already found in the decontamination formulation. The sorbent additive may comprise a single compound, or a blend of different compounds. For example, in some foaming embodiments of DF-200, polyethlyene glycol (e.g., PEG 8000 or Carbowax 8000) is used as a viscosity builder for the foam. Since PEG 8000 is typically provided as a fine powder and is essentially anhydrous, then it can also serve as some (or all) of the sorbent additive for "drying out" liquid ingredients.

Some examples of suitable compounds that may be used as the sorbent additive, either alone or in various combinations, according to the present invention, are listed in Table 1.

TABLE 1

| Sorbent Additives |
| --- |
| Sodium carbonate |
| Sodium bicarbonate |

TABLE 1-continued

Sorbent Additives

Potassium carbonate
Potassium bicarbonate
Calcium carbonate
Potassium silicate
Precipitated silicates
Percarbonates
Amorphous silica (fumed silica)
Sodium Citrate
Dendritic Salt (e.g., sea salt)
Citric Acid
Polyethylene Glycols, (e.g., PEG 8000)
Urea
Polyols (e.g., Sorbitol, Mannitol)

Some examples of suitable polyols that may be used as a sorbent additive are listed in Table 2.

TABLE 2

Polyol Sorbent Additives

Sorbitol,
Mannitol,
Hydrogenated Starch Hydrolysates (HSH),
Maltitol,
Zylitol,
Lactitol Monohydrate,
Anhydrous Isomalt,
Erythritol, and
Polydextrose.

The polyols listed above are sugar-free sweeteners. They are carbohydrates, but they are not sugars. Chemically, polyols are considered polyhydric alcohols or "sugar alcohols" because part of the structure resembles sugar and part is similar to alcohols. However, these sugar-free sweeteners are neither sugars nor alcohols, as those words are commonly used. They are derived from carbohydrates whose carbonyl group (e.g., aldehyde or ketone, reducing sugar) has been reduced to a primary or secondary hydroxyl group.

The most widely used polyols in the food industry are sorbitol, mannitol, and malitol. Sorbitol is derived from glucose; mannitol from fructose; and malitol from high maltose corn syrup. Sorbogem™ and Mannogem™ are product names for sorbitol and mannitol sold by SPI Polyols, Inc., which are available in a wide range of particle size, down to fine sizes (i.e., Sorbogem Fines™).

Sorbitol is a hexahydric alcohol ($C_6H_{14}O_6$) corresponding to glucose, and has a molecular weight of 182.2. It occurs naturally, and can be produced by the hydrogenation of glucose syrup in the presence of Raney Nickel Catalyst. Some synonyms for sorbitol include: cholaxine, clucitol, diakarmon, gulitol, 1-gulitol, karion, nivitin, sionit, sorbicolan, sorbite, d-sorbitol, sorbo, sorbol, sorbostyl, sorvilande. Sorbitol has a CAS No. 50-70-4 and an EC No. 200-061-5.

Alternatively, the sorbent additive may be selected to be a "G.R.A.S." material, meaning that it is Generally Accepted As Safe to be used in this and other applications.

Alternatively, the sorbent additive may comprise amorphous silica (i.e., fumed silica). Amorphous silica, which is water-insoluble, is commercially available from the Cabot Corporation under the trade name CAB-O-SIL® in a wide variety of particle sizes, surface areas, bulk densities, and pour densities. CAB-O-SIL® powders are untreated, high-purity, amorphous fumed silicas manufactured by high temperature hydrolysis of chlorosilanes in a hydrogen/oxygen flame. They have extremely small particle sizes, enormous surface areas (from 130-380 $m^2/g$), and can form three-dimensional branched chain aggregates with a length of approximately 0.2-0.3 microns. Further agglomeration takes place during manufacturing to yield a fine, white fluffy powder with an agglomerate size of less than about 44 microns (325 US Mesh).

When amorphous silica is used as an optional sorbent additive in the present invention, the dispersed amorphous silica can create a gel, which helps to increase the contact time. Amorphous silica is chemically un-reactive in DF-100/200 formulations, and, thus, does not change its performance against chemical and biological agents when used at relatively low concentrations.

A first example of an aqueous decontamination formulation for disinfection and sterilization applications, according to the present invention, is shown below:

Formulation #1

50 g of 8% Hydrogen Peroxide Solution
8 g Diacetin
6 g Ethanol
7 g Potassium Carbonate
29 g Deionized Water The pH of this formulation is 9.60. The total amount is 100 grams. The hydrogen peroxide concentration in this formulation is 4%.

Spore kill tests were performed on Formulation #1 using Bacillus globigii spores. Spores (initial concentration of $3.4 \times 10^7$ CFU/ml) were exposed to the formulation for contact times of 15 minutes and 60 minutes. No spore growth was observed on any culture plates after either of the contact times. This corresponds to 7-log kill in this formulation.

A second example, according to the present invention, is shown below:

Formulation #2

50 g of 8% Hydrogen Peroxide Solution
8 g Diacetin
7 g Potassium Carbonate
35 g Deionized Water The initial pH of this formulation was 9.23. Potassium Hydroxide was added to bring the pH to 9.53. The total amount is 100 grams. The hydrogen peroxide concentration in this formulation is 4%.

Spore kill tests were performed on Formulation #2 using Bacillus globigii spores. Spores (initial concentration of $4.4 \times 10^7$ CFU/ml) were exposed to the formulation for contact times of 15 minutes and 60 minutes. No spore growth was observed on any culture plates after either of these contact times. This corresponds to 7-log kill of the spores in this formulation.

To investigate the beneficial effects of using a bleaching activator, spore kill tests were performed on a simplified formulation without a bleaching activator containing 4% hydrogen peroxide, 5% potassium bicarbonate, and 91% water. These tests showed only 3-log kill in this formulation after a 60 minute contact time, clearly demonstrating the increased efficacy obtained when a bleaching activator (e.g., diacetin) is used.

In Formulations #1 and #2, the cationic surfactant, benzalkonium chloride, was eliminated because of the previously mentioned problems with leaving a residue upon drying, and also because it is not approved for use on surfaces that contact food (unless at very low concentrations, less than 400 mg/l).

Next, we present two examples of the present invention that do use a cationic surfactant (i.e., benzalkonium chloride), and that replaces the potassium carbonate base/buffer with an alternative bass/buffer (i.e., potassium acetate). Two advantages of potassium acetate over potassium carbonate are that (1) acetates tend to be even less corrosive than carbonate (which is only slightly corrosive itself), and (2) it serves as an antifreeze agent and crystal de-icer in aqueous solutions. However, potassium acetate is a much weaker base, so the final pH of the made-up formulation is around 8.0 (which is preferred over the higher pH of ~9.5). The two examples that utilize potassium acetate are shown below:

Formulation #3

50 g of 8% Hydrogen Peroxide Solution
8 g Diacetin
20 g Potassium Acetate
4 g Benzalkonium Chloride
18 g Propylene Glycol The initial pH of this formulation was 7.82. The total amount is 100 grams. No pH adjustment was made. The hydrogen peroxide concentration in this formulation is 4%.

Spore kill tests were performed on Formulation #3 using *Bacillus globigii* spores. Spores with initial concentrations of $1.08 \times 10^8$ CFU/ml and $9.6 \times 10^7$ CFU/ml were exposed to the formulation for contact times of 15 minutes and 60 minutes, respectively. No spore growth was observed on any culture plates after either of these contact times. This corresponds to 7 to 8-log kill of the spores in this formulation.

Formulation #4

50 g of 8% Hydrogen Peroxide Solution
6 g Deionized Water
4 g Diacetin
20 g Potassium Acetate
2 g Benzalkonium Chloride
18 g Propylene Glycol The initial pH of this formulation was 7.54. No pH adjustment was made. The total amount is 100 grams. The hydrogen peroxide concentration in this formulation is 4%.

Spore kill tests were performed on Formulation #4 using *Bacillus globigii* spores. Spores with initial concentrations of $1.19 \times 10^8$ CFU/ml and $1.56 \times 10^8$ CFU/ml were exposed to the formulation for contact times of 15 minutes and 60 minutes, respectively. No significant spore growth was observed on any culture plates after either of these contact times. This corresponds to 8-log kill of the spores in this formulation.

A fifth example, according to the present invention, is shown below:

Formulation #5

0.5-60% reactive compound
1-10% bleaching activator
3-30% inorganic base
0-5% cationic surfactant
0-10% ethanol
0-20% freeze-point depressant
water (remainder)

In formulation #5, the reactive compound may comprise hydrogen peroxide; the bleaching activator may comprise glycerol diacetate or propylene glycol diacetate; the inorganic base may comprise potassium acetate or potassium carbonate; the cationic surfactant may comprise benzalkonium chloride; and the freeze-point depressant may comprise propylene glycol.

A sixth example, according to the present invention, is shown below:

Formulation #6

0.5-60% hydrogen peroxide
1-10% glycerol diacetate or propylene glycol diacetate
3-10% potassium carbonate
0-10% ethanol
water (remainder)

Optionally, Formulation #6 may comprise no amount of a cationic surfactant (i.e., benzalkonium chloride).

A seventh example, according to the present invention, is shown below:

Formulation #7

0.5-60% hydrogen peroxide
1-10% glycerol diacetate or propylene glycol diacetate
5-30% potassium acetate
0-20% proplyene glycol
water (remainder)

Optionally, Formulation #7 may comprise no amount of a carbonate salt (i.e., potassium carbonate).

Two-Part Kit System

The decontamination formulations of the present invention may be packaged as a two-part kit system (i.e., Part A and Part B) kit system. When all of the water is "prepackaged" in either of Part A or Part B, the mixing of the formulation for use can be accomplished in a very short time since it only consists of two parts. Therefore, it could be deployed very easily and rapidly at the scene of an incident involving biological pathogens or agents. This configuration is ideal for use the civilian first responder (firefighter, HazMat units, police officers, and others who would be the first to arrive at the location of a CBW attack). However, it is heavier to store and carry than other kit configurations that must add water in the field. Although it is not required, all of the organic ingredients may be placed in Part A, and all of the inorganic ingredients may be placed in Part B.

A first example of a two-part kit system is shown below:

Two-Part Kit System, Example #1

Part A (organic components)
  bleaching activator
Part B (inorganic components)
  reactive compound
  inorganic base
  water Optionally, Part A may additionally comprise: solubilizing compounds, cationic surfactants, cationic hydrotropes, solvents, fatty alcohols, freeze-point depressants, water-soluble polymers, foam stabilizers, pH buffers, corrosion inhibitors, sorbent additives for drying out liquid components, and combinations thereof. Optionally, Part B may comprise pH buffers and sorbent additives. The inorganic base may comprise potassium acetate or potassium tetraborate.

A second example of a two-part kit system is shown below (wherein the total amount of solution when Parts A and B are mixed together equals 100 grams):

Two-Part Kit System, Example #2

Part A (organic components)
   1-10 grams of a bleaching activator
   0-4 grams of a cationic surfactant
   0-2 grams of a cationic hydrotrope
   0-20 grams of a freeze-point depressant
   0-0.6 grams of a fatty alcohol
   0-2 grams of a solvent
   0-6 grams of a water-soluble polymer
   0-6 grams of an organic base
Part B (inorganic components)
   3-70 grams of 8% hydrogen peroxide solution
   5-20 grams of an inorganic base
   sufficient water to make up 100 grams of made-up solution.

In this second example of a two-part kit system, the bleaching activator may comprise glycerol diacetate or propylene glycol diacetate; the cationic surfactant may comprise benzalkonium chloride; the inorganic base may comprise potassium acetate (which serves as a base/buffer and antifreeze agent); the freeze-point depressant may comprise propylene glycol; the fatty alcohol may comprise 1-dodecanol; the solvent may comprise diethylene glycol monobutyl ether and isobutanol; the water-soluble polymer may comprise poly-ethoxylated glycerine; the organic base may comprise triethanolamine; and the inorganic base may comprise potassium acetate.

A third example of a two-part kit system is shown below (wherein the total amount of solution when Parts A and B are mixed together equals 100 grams):

Two-Part Kit System, Example #3

Part A (organic components)
   2 g Variquat 80MC
   1 g Adogen 477
   10 g Propylene Glycol
   0.4 g 1-Dodecanol
   0.8 g Diethylene Glycol Monobutyl Ether
   0.5 g Isobutanol
   4 g Poly-Ethoxylated Glycerine [POE (12)]
   4 g Glycerol Diacetate (Diacetin)
Part B (inorganic components)
   50 g 8% Hydrogen Peroxide Solution
   15 g Potassium Acetate
   12.3 g De-ionized Water Mix Part A into Part B. The final pH (after mixing) should be between 7.5 and 8.0.

In Example #3, Part A contains all organic components and Part B contains all inorganic components and water. The peroxide activator (glycerol diacetate in Part A) is protected from water and hydrogen peroxide, both of which are packaged in Part B. In order to configure DF-200 as a two-part (or binary) system, three fundamental changes were made to standard three-part DF-200 formulations.

1. Elimination of Potassium Carbonate and Bicarbonate—these serve as a base and pH buffer in the three-part DF-200 configuration. In the two-part configuration, these constituents were replaced by potassium acetate. Potassium acetate is also a base and a pH buffer. Carbonate and bicarbonate were eliminated because it would be necessary to place them in Part B (since they are inorganic) but this is not possible because they react with hydrogen peroxide. Testing of this two-part configuration demonstrated that a mixture of peroxide and acetate is stable, as will be described below. Potassium acetate also allows for additional effects that carbonates, etc. cannot provide.

2. Elimination of Celquat SC-240C—The water soluble polymer Celquat SC-240C was replaced by an organic viscosity- booster, poly-ethoxylated glycerine. Since it is water soluble, Celquat SC-240C would have to be placed in Part B where it would react with and degrade the hydrogen peroxide over time. Poly-ethoxylated glycerol (e.g., POE-12) is placed in Part A with the other organic constituents. POE-12 also maintains its working function over a larger range of environments (e.g., pH, Temp, etc.) than do others in this family.

3. Higher Glycerol Diacetate (peroxide activator) Concentration—It should be noted that the pH of this configuration (Example #3) is lower (~7.5) than the three-part DF-200 configuration (~9.6). The higher pH in the original three-part configuration is necessary to decontaminate certain chemical agents (e.g., VX); and to produce a high concentration of the peracetate molecule (the pH for the deprotonation reaction of hydrogen peroxide is 9.6—therefore, formation of the OOH$^-$ species, which reacts with glycerol diacetate to form peracetate, is optimal at pH values near 10). The higher pH is not necessary for kill of biological pathogens. A pH between 7.5-8.0 will achieve a very high level kill of microorganisms (including bacterial spores), as shown below. The lower concentration of the peracetate molecule (at this lower pH) is compensated for by adding a higher concentration of glycerol diacetate, which drives the peracetate production reaction to the right, thereby producing more peracetate.

A fourth example of a two-part kit system is shown below (wherein the total amount of solution when Parts A and B are mixed together equals 100 grams):

Two-Part Kit System, Example #4

| Part A | Part B |
|---|---|
| 2 g Variquat 80MC | 50 g 8% Hydrogen Peroxide Solution |
| 4 g Glycerol Diacetate | 20 g Potassium Acetate |
| 18 g Propylene Glycol | 6 g De-ionized Water |

The pH (after mixing) was ~7.5. Spore kill tests were performed on the two-part DF-200 formulation of Example #4 using *Bacillus globigii* spores. Spores (initial concentration of 1.2×10$^8$ CFU/ml) were exposed to the formulation for contact times of 15 minutes and 60 minutes. No significant spore growth was observed on any culture plates after either of these contact times. This corresponds to 7-log kill of the spores in this formulation.

In order to assess the stability of the individual parts in these two-part kit systems, the solution containing hydrogen peroxide and potassium acetate (i.e., Part B in the two-part DF-200 formulation) was tested for the presence of hydrolysis by-products, peracetate formation, and peroxide stability.

The tests were conducted at both room temperature (~23° C.) and at an elevated temperature (~80° C.). There were no hydrolysis by-products detected in the solution, which was verified by several testing methodologies. No peracetate formation or degradation of the peroxide was detected, either. The addition of the potassium acetate to the peroxide/water blend has no apparent effect in destabilizing the $H_2O_2$ solution (Part B) above what is seen in a solution of commercially-available stabilized $H_2O_2+H_2O$. In fact, potassium acetate is used by some companies as a stabilizer of peroxide (albeit at much lower concentrations).

Note that an organic base, such as triethanolamine (TEA), can also be added to any of the 2-part kit configurations to increase the pH, and to provide corrosion protection. TEA is a common ingredient in many cosmetics including some shampoos. Because TEA is an organic, it is placed in Part A.

Another example of a two-part configuration for DF-200, Example #5, is shown below:

Two-Part Kit System, Example #5

| Part A: | Part B: |
|---|---|
| 2 g Variquat 80MC | 50 g 8% Hydrogen Peroxide Solution |
| 1 g Adogen 477 | 24.3 g De-Ionized Water |
| 10 g Propylene Glycol | |
| 0.4 g 1-Dodecanol | |
| 0.8 g Diethylene Glycol Monobutyl Ether | |
| 0.5 g Isobutanol | |
| 4 g Poly-Ethoxylated Glycerine [POE (12)] | |
| 4 g Glycerol Diacetate (Diacetin) | |
| 3 g Triethanolamine (TEA) | |

In this example, potassium acetate was removed and replaced with the organic base, triethanolamine (TEA). Note that this configuration contains only one inorganic constituent (i.e., $H_2O_2$). The only base is the organic constituent, TEA.

Another example of a two-part configuration for DF-200, Example #6, is shown below:

Two-Part Kit System, Example #6

| Part A: | Part B: |
|---|---|
| 2 g Variquat 80MC | 50 g 8% Hydrogen Peroxide Solution |
| 4 g Glycerol Diacetate | 24.3 g Deionized Water |
| 18 g Propylene Glycol | |
| 3 g Triethanolamine | |

The pH (after mixing) was ~8.5. Spore kill tests were performed using *Bacillus globigii* spores. Spores (initial concentration of ~$1.0 \times 10^8$ CFU/ml) were exposed to the formulation for contact times of 15 minutes and 60 minutes. Interestingly, no significant spore kill was achieved after either of these contact times. These results suggest that the presence of an inorganic base and/or buffer (e.g., potassium, sodium, ammonium, calcium, or magnesium salts of carbonate, bicarbonate, hydroxide, sulfate, phosphate, borate, and/or acetate) helps to achieve high rates of spore kill in DF-200.

Optionally, the two-part kit systems may comprise no amount of a cationic surfactant. Alternatively, the two-part kit systems may comprise no amount of benzalkonium chloride. Alternatively, the two-part kit systems may comprise no amount of a cationic surfactant.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents.

What is claimed is:

1. An aqueous decontamination formulation for use in disinfection and sterilization, said formulation consisting of (by weight percentage):
    0.5-60% reactive compound selected from the group consisting of nucleophilic compounds and oxidizing compounds;
    1-10% water-soluble bleaching activator selected from the group consisting of ethylene glycol diacetate, propylene glycol monomethyl ether acetate, methyl acetate, diethylene glycol monoethyl ether acetate, glycerol acetate (monoacetin), glycerol diacetate (diacetin), glycerol triacetate (triacetin), acetylcholine chloride, 4-cyanobenzoic acid, propylene glycol diacetate, and combinations thereof;
    3-30% inorganic base; and
    water (remainder);
    wherein:
    said reactive compound comprises hydrogen peroxide;
    said bleaching activator comprises glycerol diacetate or propylene glycol diacetate; and
    said inorganic base comprises potassium acetate.

2. An aqueous decontamination formulation for use in disinfection and sterilization, said formulation consisting of:
    a reactive compound selected from the group consisting of nucleophilic compounds and oxidizing compounds;
    a water-soluble bleaching activator selected from the group consisting of ethylene glycol diacetate, propylene glycol monomethyl ether acetate, methyl acetate, diethylene glycol monoethyl ether acetate, glycerol acetate (monoacetin), glycerol diacetate (diacetin), glycerol triacetate (triacetin), acetylcholine chloride, 4-cyanobenzoic acid, propylene glycol diacetate, and combinations thereof;
    an inorganic base;
    water; and
    one or more sorbent additives selected from the group consisting of sodium carbonate, sodium bicarbonate, potassium carbonate, potassium bicarbonate, calcium carbonate, potassium silicate, precipitated silicates, percarbonates, amorphous silica, fumed silica, sodium citrate, dendritic salt (sea salt), citric acid, polyethylene glycol, PEG 8000, urea, and polyols;
    wherein said sorbent additive comprises one or more polyol compounds selected from the group consisting of sorbitol, mannitol, hydrogenated starch hydrolysates (HSH), maltitol, zylitol, lactitol monohydrate, anhydrous isomalt, erythritol, and polydextrose.

3. The formulation of claim 2, wherein the inorganic base is selected from the group consisting of potassium carbonate, potassium bicarbonate, potassium hydroxide, potassium sulfate, potassium phosphate (dibasic or tribasic), potassium borate, potassium tetraborate, potassium acetate, sodium carbonate, sodium bicarbonate, sodium hydroxide, sodium sulfate, sodium phosphate (dibasic or tribasic), sodium borate, sodium acetate, ammonium carbonate, ammonium bicarbonate, ammonium hydroxide, ammonium sulfate, ammonium phosphate (dibasic or tribasic), ammonium borate, ammonium acetate, calcium carbonate, calcium bicarbonate, calcium hydroxide, calcium sulfate, calcium phosphate (dibasic or tribasic), calcium borate, calcium acetate, magnesium carbonate, magnesium bicarbonate, magnesium hydroxide, magnesium sulfate, magnesium phosphate (dibasic or tribasic), magnesium borate, magnesium acetate, sodium percarbonate, ammonium hydrogen bicarbonate and lithium bicarbonate, and combinations thereof.

4. An aqueous decontamination formulation for use in neutralization of a toxant, said formulation consisting of (by weight percentage):
   0.5-60% hydrogen peroxide;
   1-10% glycerol diacetate or propylene glycol diacetate;
   3-10% potassium carbonate; and
   water (remainder).

5. An aqueous decontamination formulation for use in neutralization of a toxant, said formulation consisting of (by weight percentage):
   0.5-60% hydrogen peroxide;
   1-10% glycerol diacetate or propylene glycol diacetate;
   5-30% potassium acetate; and
   water (remainder).

6. An aqueous decontamination formulation for use in disinfection and sterilization, said formulation consisting of:
   a reactive compound selected from the group consisting of nucleophilic compounds and oxidizing compounds;
   a water-soluble bleaching activator selected from the group consisting of ethylene glycol diacetate, propylene glycol monomethyl ether acetate, methyl acetate, diethylene glycol monoethyl ether acetate, glycerol acetate (monoacetin), glycerol diacetate (diacetin), glycerol triacetate (triacetin), acetylcholine chloride, 4-cyanobenzoic acid, propylene glycol diacetate, and combinations thereof;
   an inorganic base; and
   water;
wherein said water-soluble bleaching activator is acetylcholine chloride or 4-cyanobenzoic acid.

* * * * *